United States Patent [19]
Thorén

[11] Patent Number: 5,129,893
[45] Date of Patent: Jul. 14, 1992

[54] SANITARY NAPKIN

[75] Inventor: Agneta Thorén, Gothenburg, Sweden

[73] Assignee: Molnlycke AB, Gothenburg, Sweden

[21] Appl. No.: 368,397

[22] PCT Filed: Dec. 17, 1987

[86] PCT No.: PCT/SE87/00612

§ 371 Date: Jun. 2, 1989

§ 102(e) Date: Jun. 2, 1989

[87] PCT Pub. No.: WO88/04547

PCT Pub. Date: Jun. 30, 1988

[30] Foreign Application Priority Data

Dec. 19, 1986 [SE] Sweden ................ 8605498

[51] Int. Cl.$^5$ ................................ A61F 13/56
[52] U.S. Cl. .................. 604/385.2; 604/385.1; 604/393
[58] Field of Search ............ 604/385.1, 385.2, 393, 604/394

[56] References Cited

U.S. PATENT DOCUMENTS

| | | |
|---|---|---|
| 4,324,245 | 4/1982 | Mesek et al. |
| 4,631,062 | 12/1986 | Lassen et al. ............ 604/393 X |
| 4,661,102 | 4/1987 | Shikata et al. ............ 604/385.2 |
| 4,662,877 | 5/1987 | Williams .................. 604/385.2 |
| 4,692,163 | 9/1987 | Widlund et al. ........... 604/385.2 |
| 4,897,084 | 1/1990 | Ternström et al. ........ 604/385.2 |
| 4,911,701 | 3/1990 | Mavinkurve .............. 604/386 X |
| 4,935,021 | 6/1990 | Huffman et al. ........... 604/385.1 |

FOREIGN PATENT DOCUMENTS

| | | |
|---|---|---|
| 0155515 | 9/1985 | European Pat. Off. . |
| 3423644 | 1/1986 | Fed. Rep. of Germany ... 604/385.2 |
| 3604555 | 8/1986 | Fed. Rep. of Germany . |
| 3517192 | 11/1986 | Fed. Rep. of Germany . |
| 149646 | 5/1984 | Norway . |
| 149801 | 6/1984 | Norway . |
| 854815 | 11/1985 | Norway . |

*Primary Examiner*—David Isabella
*Assistant Examiner*—D. Willse
*Attorney, Agent, or Firm*—Young & Thompson

[57] ABSTRACT

The present invention relates to a sanitary napkin consisting of an absorbent core (1) surrounded by a casing built up of two surface layers which are joined together around the absorbent core and of which surface layers the one facing the wearer's body is liquid permeable whereas the other one (2) is liquid impermeable.

According to the invention, elastic means (5,6) are applied to the liquid impermeable surface layer (2). The resiliency afforded to the sanitary napkin in this manner will urge the napkin in its applied condition to press against the outer genitals of the wearer.

4 Claims, 2 Drawing Sheets

SANITARY NAPKIN

The present invention relates to a sanitary napkin consisting of an absorbent core enclosed in a casing which is composed of two surface layers joined together around the absorbent core and of which the surface layer facing the wearer's body is liquid permeable, whereas the surface layer facing away from the wearer's body is liquid impermeable.

The object of the invention is to minimize the risk of leakage associated with sanitary napkins.

As far as diapers are concerned, the technique of utilizing elastic for providing the absorbent core with upwardly bent portions is previously known, the absorbent core in this manner being capable of momentarily taking up larger amounts of fluid.

With regard to sanitary napkins however, this prior art method is not optimally applicable because firstly, the fluid discharged very seldomly amounts to such large quantities that it cannot be immediately absorbed by the sanitary napkin and secondly, the sanitary napkin is affixed inside the panty instead of being secured to the body of the wearer by tightening a backing sheet or the like around the abdomen, as is the case with diapers. Therefore, leakage generally does not result from a large momentarily non-absorbable volume of fluid flowing within the absorbent core and leaking out of it but instead, leakage in a sanitary napkin is more likely caused by menstrual fluid often seeping down outside the absorbent core, thereby giving rise to discoloration of panties or other garments.

The invention has for its object to diminish to a large extent the risk of leakage associated with the use of sanitary napkins. According to the invention, this is accomplished with a sanitary napkin having the distinguishing features set forth in the appended Claim 1.

By the action of elastic means applied to the outside of the sanitary napkin, the napkin will be urged to exert a resilient pressure onto the outer genitals of the wearer, preventing in this manner any menstrual fluid from seeping down outside the absorbent core.

In order to facilitate the understanding of the invention, an embodiment thereof will now be described with the aid of the accompanying drawings, of which FIG. 1 is a view of the inventive sanitary napkin as seen from the side facing away from the wearer;

Figure 1:
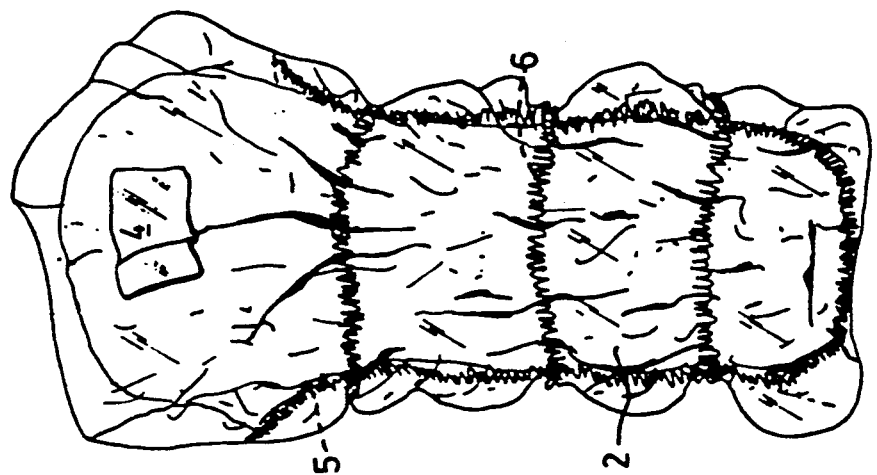

The sanitary napkin illustrated in the figures consists of an absorbent core 1 which is enclosed in a casing composed of two surface layers 2, 3, said layers being joined together in a suitable manner around the absorbent core. The suitable layer 2 is liquid impermeable and is placed during use to face away from the wearer's body. Furthermore, a binder coating with only a limited extension is applied to this surface layer for the sake of securing the sanitary napkin inside the wearer's panty. The binder coating is covered in a conventional manner with a piece of releasable protective tape 4. The surface layer 3 is liquid permeable and thus intended for placement in close contact with the wearer's body on application of the sanitary napkin in the panty.

As is most clearly evident from FIG. 1 showing the sanitary napkin in a planar condition, the napkin is provided with prestretched elastic means 5, 6 affixed to the side of the surface layer 2 facing the absorbent core, for example by gluing. Said elastic means can consist of ribbons or threads 5 extending along the absorbent core and outside its two long sides, and transverse threads 6 interconnecting the longitudinal threads 5.

Figure 2:
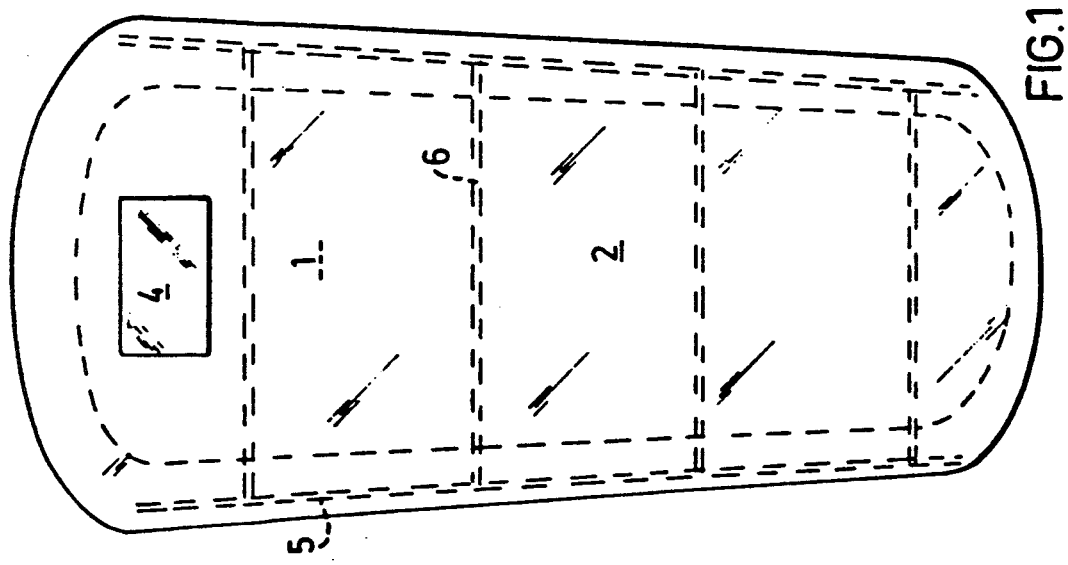
FIG. 2 is a view similar to that of FIG. 1 but showing the sanitary napkin in its freely distorted state.
Figure 3:
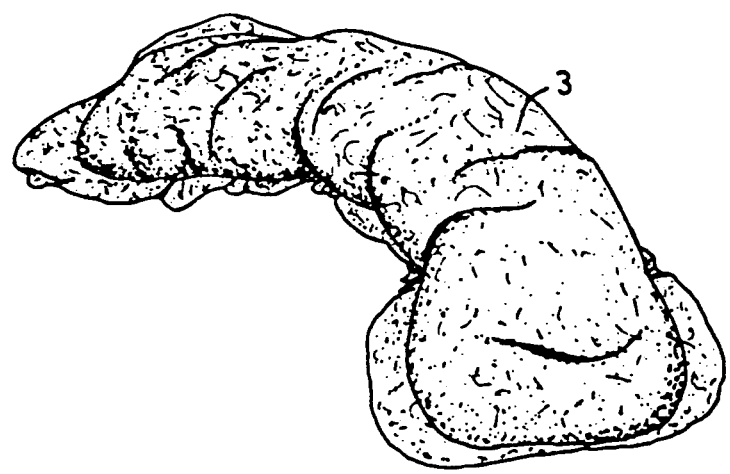
FIG. 3 is a perspective view of the inventive sanitary napkin in its state of distortion as seen obliquely from above and having its body contacting side turned upwards.
Figure 4:
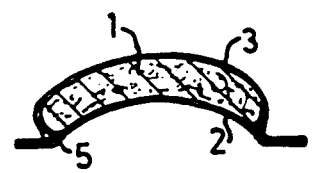
FIG. 4 is a cross sectional view of the sanitary napkin shown in FIG. 3.

FIGS. 2-4 illustrate a sanitary napkin according to FIG. 1 in a freely destorted state, which is the configuration the sanitary napkin is imagined to assume unless exposed to any amount of stress whatsoever. In its state of free distortion, the napkin will thus assume an arcuate shape both longitudinally and transversely due to the effect of elasticity.

In use, i.e. when attached inside a panty which is then pulled up to bear against the crotch region of the wearer, the inventive sanitary napkin will assume a more planar configuration than that shown in the figures due to its pressure against the outer genitals of the wearer. If for some reason the panty should be displaced in relation to the wearer's body, for example on back and forth shuffling movements in a cinema chair causing the portion of the panty placed next to the genitals to gap in relation thereto, the napkin will however curve from its relatively planar shape into the bent shape assumed by the napkin in its freely distorted state, maintaining in this manner its initial contact with the outer genitals.

Thus, the purpose of the elastic is to achieve a resiliency intended to secure a safe contact between the sanitary napkin and the outer genitals of the wearer while simultaneously permitting a "planar" fit of the napkin on exterior pressure forces arising for example when riding a bicycle. With the inventive article there is thus attained a more or less arcuate sanitary napkin, the curvature varying with the distance between genitals and panty, which distance may deviate in response to displacements of the panty. The enhanced conformability of the relationship between the napkin and the wearer's body will make the additional support of the panty afforded by trousers superfluous, the inventive sanitary napkin thereby making is possible to wear a skirt without increasing the risk of leakage.

The embodiment shown can of course be modified in numerous respects within the scope of the inventive idea. For example, the sanitary napkin may be provided with only transverse elastic. The absorbent core, and thereby the entire napkin, can be given other configurations. Furthermore, the distance between the transverse elastic means may differ, as could also the extension of the longitudinal means for example in order to achieve portions of the absorbent core resistant to distortion from its planar state. The invention is therefore to be restricted solely by the contents of the appended patent claims.

I claim:

1. A sanitary napkin consisting of an absorbent core (1) which is enclosed in a casing composed of two surface layers (2,3) joined together around the absorbent core and of which the surface layer (3) facing the wearer's body is liquid permeable, whereas the other layer (2) is liquid impermeable, characterized in that elastic means (5,6) are applied to the liquid impermeable surface layer (2), and that the elastic means are prestretched and intended to resiliently distort the sanitary napkin such that the side thereof facing the wearer's outer genitals will assume a convex shape, this shape being flattened out on the occurrence of contact pressure against the napkin but resiliently resuming its curved shape for pressing the convex surface against the outer genitals of the wearer when the contact pressure is momentarily suspended.

2. A sanitary napkin according to claim 1, characterized in that the elastic means (6) extend in the transverse direction of the napkin.

3. A sanitary napkin according to claim 1, characterized in that the elastic means (5,6) extend in the longitudinal as well as in the transverse direction of the napkin.

4. A sanitary napkin comprising:
 (a) an absorbent element having longitudinally extending sides, transverse ends, a body-facing side covered by a fluid pervious member, and an undergarment facing side covered by fluid impervious backing layer, and
 (b) an elastic strip disposed in tension transversely across said absorbent element and affixed to said napkin at at least two points to impart a convex shape toward the body of the user to said body-facing side.

* * * * *